(12) United States Patent
Karimi et al.

(10) Patent No.: US 11,022,597 B2
(45) Date of Patent: Jun. 1, 2021

(54) FLUID SENSING SYSTEM USING PLANAR RESONATORS

(71) Applicants: Saudi Arabian Oil Company, Dhahran (SA); King Abdullah University of Science and Technology, Thuwal (SA)

(72) Inventors: Muhammad Akram Karimi, Thuwal (SA); Atif Shamim, Thuwal (SA); Muhammad Arsalan, Dhahran (SA)

(73) Assignees: Saudi Arabian Oil Company, Dhahran (SA); King Abdullah University of Science and Technology, Thuwal (SA)

( * ) Notice: Subject to any disclaimer, the term of this patent is extended or adjusted under 35 U.S.C. 154(b) by 342 days.

(21) Appl. No.: 15/984,469

(22) Filed: May 21, 2018

(65) Prior Publication Data

US 2019/0353633 A1  Nov. 21, 2019

(51) Int. Cl.
*G01N 33/28* (2006.01)
*E21B 34/06* (2006.01)
*E21B 49/08* (2006.01)
*G01N 22/00* (2006.01)

(52) U.S. Cl.
CPC ......... *G01N 33/2847* (2013.01); *E21B 34/06* (2013.01); *E21B 49/087* (2013.01); *G01N 22/00* (2013.01); *E21B 49/0875* (2020.05)

(58) Field of Classification Search
CPC .... G01N 33/2847; G01N 22/00; E21B 34/06; E21B 49/087; E21B 49/0875
USPC .......................................................... 73/64
See application file for complete search history.

(56) References Cited

U.S. PATENT DOCUMENTS

| | | | |
|---|---|---|---|
| 4,490,676 A | 12/1984 | Davis, Jr. et al. | |
| 4,499,418 A | 2/1985 | Helms et al. | |
| 4,543,821 A | 10/1985 | Davis, Jr. | |
| 5,341,101 A | 8/1994 | Maerefat et al. | |
| 5,389,883 A | 2/1995 | Harper | |
| 5,485,743 A | 1/1996 | Taherian et al. | |
| 5,493,226 A | 2/1996 | Honarpour et al. | |
| 6,330,831 B1 * | 12/2001 | Lynnworth | G01F 1/662 73/861.28 |

(Continued)

FOREIGN PATENT DOCUMENTS

| | | | | |
|---|---|---|---|---|
| GB | 2365978 A * | 2/2002 | ......... | G01N 33/2823 |
| WO | WO-2017/040102 A1 | 3/2017 | | |
| WO | WO-2018/052865 A1 | 3/2018 | | |

OTHER PUBLICATIONS

Agar Corporation, OW-200 Series Oil/Water Meters Liquid/Liquid Concentration, Process Measurement & Control Solutions, 3 pages [Retrieved Online Jun. 19, 2018]. URL: http://www.agarcorp.com/literature/ow200.html.

(Continued)

*Primary Examiner* — Alexander A Mercado
*Assistant Examiner* — Monica S Young
(74) *Attorney, Agent, or Firm* — Choate, Hall & Stewart LLP; Peter A. Flynn; Jialan Zhang

(57) ABSTRACT

An example system includes a core comprised of a dielectric material; a planar resonator on the core; a conduit containing the core and the planar resonator, with the conduit including an electrically-conductive material; and a coupling that is electrically-conductive and that connects the planar resonator to the conduit to enable the conduit to function as an electrical ground for the planar resonator.

18 Claims, 14 Drawing Sheets

(56) References Cited

U.S. PATENT DOCUMENTS

| | | | | |
|---|---|---|---|---|
| 6,525,540 | B1* | 2/2003 | Kong | G01S 7/03 |
| | | | | 324/338 |
| 6,915,707 | B2* | 7/2005 | Nyfors | G01F 1/40 |
| | | | | 73/861.63 |
| 8,640,529 | B2* | 2/2014 | Sinha | G01F 1/66 |
| | | | | 73/61.45 |
| 9,335,273 | B2 | 5/2016 | Botto et al. | |
| 9,650,891 | B2 | 5/2017 | Reid et al. | |
| 9,804,105 | B2 | 10/2017 | Karimi et al. | |
| 2007/0240498 | A1* | 10/2007 | Scott | G01N 33/2847 |
| | | | | 73/61.43 |
| 2010/0148804 | A1* | 6/2010 | Jakoby | G01F 1/662 |
| | | | | 324/663 |
| 2013/0033272 | A1* | 2/2013 | Folgeroe | G01N 22/00 |
| | | | | 324/637 |
| 2014/0182737 | A1* | 7/2014 | Jones | G01F 1/32 |
| | | | | 138/177 |
| 2014/0323363 | A1 | 10/2014 | Perriat et al. | |
| 2015/0218941 | A1* | 8/2015 | Clarke | G01F 1/56 |
| | | | | 324/324 |
| 2015/0346117 | A1* | 12/2015 | Nyfors | G01F 1/58 |
| | | | | 324/633 |
| 2015/0376493 | A1 | 12/2015 | Huh et al. | |
| 2017/0010209 | A1* | 1/2017 | Arsalan | G01N 21/17 |
| 2017/0059492 | A1* | 3/2017 | Karimi | G01N 33/2823 |
| 2017/0191977 | A1 | 7/2017 | Nyfors | |
| 2017/0248506 | A1 | 8/2017 | Gupta et al. | |
| 2017/0350830 | A1* | 12/2017 | Karimi | G01N 33/2847 |
| 2017/0361376 | A1 | 12/2017 | Murugesan et al. | |
| 2018/0011033 | A1 | 1/2018 | Karimi et al. | |
| 2018/0045662 | A1* | 2/2018 | Nyfors | G01N 33/2823 |
| 2019/0094405 | A1* | 3/2019 | Itskovich | G01V 3/10 |

OTHER PUBLICATIONS

Al-Taweel, A. B. and Barlow, S. G., Field Testing MultiPhase Meters, Society of Petroleum Engineers Inc. SPE 56583, 16 pages (1999).

Alvarado, F.E.,et al., Visualization of three phases in porous media using micro computed tomography, paper SCA2003-21 presented at the International Symposium of Society of Core Analysts, Pau, France (Sep. 21-24, 2003).

Amyx, J.W. et al., Petroleum Reservoir Engineering, Physical Properties, McGraw Hill Book Co., New York, Indian Edition, 629 pages (1960).

Ayub, M. and Bentsen, R. G., An Apparatus for Simultaneous Measurement of Dynamic Saturation and Capillary Pressure Profiles, Paper 99-72: presented at the CSPG and Petroleum Society Joint Convention, Digging Deeper, Finding a Better Bottom Line, Calgary, Alberta, Canada, 13 pages (Jun. 14-18, 1999).

Ayub, M. and Bentsen, R. G., Measurement of Dynamic Saturation Profiles, Journal of Canadian Petroleum Technology, 39(9): 54-61 (2000).

Bail, P.T. and Marsden, S.S., Saturation distribution in a linear system during oil displacement, Producers Monthly, 21(8): 22-32 (1957).

Brost, D.F. and Davis, L.A., Determination of oil saturation distribution in field cores by microwave spectroscopy, SPE 10110, presented at the 56th Annual Fall Technical Conference and Exhibition, Society of Petroleum Engineers of AIME, San Antonio, TX, 19 pages (Oct. 5-7, 1981).

Caudle, B.H. et al., Further developments in the laboratory determination of relative permeabilities, Trans. AIME, 192: 145-150 (1951).

Chatenever, A. and Calhoun, J.C. Jr., Visual examinations of fluid behavior in porous media—Part 1, Trans. AIME, 195: 149-156 (1952).

Craig, F.F., Jr., The Reservoir Engineering Aspects of Waterflooding, Monograph vol. 3 of the Henry L. Doherty Series, Millet the Printer, Dallas, TX, 141 pages (1971).

Davis, L.A. Jr., Computer-controlled measurement of laboratory areal flood saturation distributions, SPE 12037, presented at the 58th Annual Fall Technical Conference and Exhibition, Society of Petroleum Engineers of AIME, San Francisco, CA, 8 pages (Oct. 5-8, 1983).

Davis, L.A. Jr., VHF electrical measurement of saturation in laboratory floods, Paper SPE No. 8847 presented at the First Joint SPE/DOE Symposium on Enhanced Oil Recovery, Tulsa, Oklahoma, 10 pages (Apr. 20-23, 1980).

Dongzhi, Z., Analysis of Multi-factor Influence on Measurement of Water Content in Crude Oil and Its Prediction Model, Proceedings of the 27th Chinese Control Conference, Kunming, Yunnan, China, 6 pages (Jul. 16-18, 2008).

Essiflo, Water Cut Meter, 5 pages [Retrieved Online Jun. 19, 2018]. URL: http://eesiflo.com/water-cut-meter.html.

Geffen, T.M. and Gladfelter, R.E., A note on the X-ray absorption method of determining fluid saturations in cores, Petroleum Transactions, AIME, 195: 322-323 (1952).

Honarpour, M. and Mahmood, S.M., Relative permeability measurements: An Overview, Journal of Petroleum Technology, SPE 18565: 963-966 (Aug. 1988).

Honarpour, M., et al., Relative Permeability of Petroleum Reservoir, CRC Press, Inc., Boca Raton, FL, USA, 154 pages (1986).

Joshi, K.K. et al., Non-destructive Microstrip Resonator Technique for the measurement of moisture / permittivity in crude oil, Proceedings of the XXVIIIth URSI General Assembly, New Delhi, India, 8 pages (2005).

Kantzas, A., Investigation of physical properties of porous rocks and fluid flow phenomena in porous media using computer assisted tomography, In Situ, 14(1): 77-132 (1990).

Karimi, M.A. et al., Design and Dynamic Characterization of an Orientation Insensitive Microwave Water-Cut Sensor, IEEE Transactions on Microwave Theory and Techniques, 66(1): 530-539 (2018).

Karimi, M.A. et al., Low Cost and Pipe Conformable Microwave-Based Water-Cut Sensor, IEEE Sensors Journal, 16(21): 7636-7645 (2016).

Laird, A.D.K. and Putman, J.A., Fluid saturation in porous media by X-ray techniques, Petroleum Transactions, AIME, 192: 275-284 (1951).

Leverett, M.G. and Lewis, W.B., Steady flow of gas-oil-water mixtures through unconsolidated sands, Petroleum Transactions, AIME, 142: 107-116 (1941).

McKerricher, G. et al., Crude Oil Water-Cut Sensing with Disposable Laser Ablated and Inkjet Printed RF Microfluidics, IMS, 3 pages (2014).

Mohamed, A.-M. O. et al., Effect of salinity and temperature on water cut determination in oil reservoirs, Journal of Petroleum Science and Engineering, 40: 177-188 (2003).

Nyfors, E. G., Cylindrical Microwave Resonator Sensors for Measuring Materials Under Flow, Helsinki University of Technology, Report S243, 181 pages (May 2000).

Parker, A. and Joshi, S., M-Flow Technologies Ltd, 16040: Non-Intrusive Water Cut Measurement Based on a Composite Construction Material Platform, UPM Forum, Upstream Production Measurement, Houston, TX, 18 pages (Feb. 24-25, 2016).

Parsons, R.W., Microwave Attenuation—A new tool for monitoring saturations in laboratory flooding experiments, Society of Petroleum Engineers Journal, 15(4): 302-310 (1975).

Roxar, Roxar Watercut meter, Product Data Sheet, Emerson Process Management, 11 pages (Apr. 4, 2016). URL: http://www2.emersonprocess.com/siteadmincenter/PM%20Roxar%20Documents/Roxar%20Watercut%20meter%20Data%20Sheet.pdf.

Schematic drawing of core-flooding setup, ResearchGate, 4 pages [Retrieved Mar. 15, 2018]. URL: https://www.researchgate.net/figure/Schematic-drawing-of-core-flooding-setup-The-isolat . . . .

Stanley, M., Magnetometers come in multiple flavors, Me and My Smarter World, NXP, 4 pages (Mar. 4, 2011). URL: <https://bloq.nxp.com/sensors/maqnetometers-come-in-multiple-flavors>. [Retrieved Apr. 18, 2018].

Sun, X. et al., Application of Nanoparticles in Enhanced Oil Recovery: A Critical Review of Recent Progress, Energies, 10(345): 33 pages (2017).

(56) References Cited

OTHER PUBLICATIONS

Swanson, B.F., Visualizing Pores and Nonwetting Phase in Porous Rock, Journal of Petroleum Technology, 10-18 (1979).
Tošic, D. and Potrebic, M., Compact Multilayer Bandpass Filter with Modified Hairpin Resonators, Journal of Microelectronics, Electronic Components and Materials, 42(2): 123-130 (2012).
Weatherford International, Water-Cut Meters, 3 pages [Retrieved Online Jun. 19, 2018]. URL: https://www.weatherford.com/en/products-and-services/production/flow-measurement/water-cut-meters.
Willhite, G.P., Waterflooding, Society of Petroleum Engineers, Richardson, TX., USA, SPE Textbook Series, vol. 3, 333 pages (1986).
Wylie, S.R. et al., RF sensor for multiphase flow measurement through an oil pipeline, Meas. Sci. Technol., 17: 2141-2149 (2006).
Yadav, G.D. et al., Microscopic distribution of wetting and nonwetting phases in sandstones during immiscible displacements, SPE Reservoir Engineering, 2: 137-147 (1987).
Yang, Y.S. et al., The Design, Development and Field Testing of a Water-Cut Meter Based on a Microwave Technique, Society of Petroleum Engineers, SPE 20697: 775-782 (1990).
International Search Report for PCT/IB2018/057352, 7 pages (dated Mar. 14, 2019).
Written Opinion for PCT/IB2018/057352, 9 pages (dated Mar. 14, 2019).
International Preliminary Report on Patentability for PCT/IB2018/057352, 14 pages (dated Aug. 31, 2020).

\* cited by examiner

FLUID SENSING SYSTEM USING PLANAR RESONATORS

TECHNICAL FIELD

This specification relates generally to example techniques for identifying content in a metal conduit using, for example, one or more planar microwave resonators that use the metal conduit as a common ground plane.

BACKGROUND

Conduits, such as metal pipes, are used to transmit content, such as fluids, in a wide range of applications. For example, in the petroleum industry, a metal pipe may transmit fluid flows comprised of oil, water, or both oil and water. In some cases, it is desirable to characterize the content that is present in a conduit. For example, in the petroleum industry, the productivity of a well may be affected by excess water in a fluid flow. In this example, therefore, knowing the amount of water in the fluid flow may allow a driller to take action.

SUMMARY

An example system includes a core comprised of a dielectric material, a planar resonator on the core, and a conduit containing the core and the planar resonator. The conduit includes an electrically-conductive material. The example system also includes a coupling that is electrically-conductive and that connects the planar resonator to the conduit to enable the conduit to function as an electrical ground for the planar resonator. The example system may include one or more of the following features, either alone or in combination.

The planar resonator may be a microwave T-resonator. The planar resonator may be a ring resonator. The planar resonator may be a spiral T-resonator. The planar resonator may include material printed onto the core. The conduit may include a pipe that is made of metal. The conduit may be configured to function as electromagnetic shielding for the planar resonator.

The system may include a computing system to obtain data from the planar resonator, to obtain a resonance frequency of the planar resonator based on the data, and to identify a content of the conduit based on the resonance frequency. The content may include fluid. Identifying the fluid may include determining a change in the resonance frequency or a quality factor of the planar resonator.

The system may include one or more additional planar resonators spatially distributed on the core. The system may include one or more additional couplings, such as metal shorting rods. Each of the additional couplings may be electrically-conductive and may be configured to connect the conduit to a corresponding additional planar resonator to enable the conduit to function as the electrical ground for the additional planar resonator. The one or more additional planar resonators may include between one additional planar resonator and seven additional planar resonators. The one or more additional planar resonators may be on different sectors of the core.

The system may include one or more metallic separators within the conduit. The one or more metallic separators may be for confining fluid within individual sectors of the core.

The system may include a computing system to obtain data from each planar resonator, to obtain a resonance frequency of each planar resonator based on at least some of the data, and to identify content in different sectors of the conduit based on the resonance frequencies and quality factors of the planar resonators.

An example method includes identifying content in a conduit comprised of electrically-conductive material. The example method includes obtaining data based on signals output from a planar resonator on a dielectric core within the conduit. The conduit is electrically coupled to the planar resonator to function as electrical ground for the planar resonator. The example method also includes determining a resonance frequency, a quality factor, or both a resonance frequency and a quality factor of the planar resonator based on the data. The resonance frequency and the quality factor correspond to the content. The method also includes identifying the content based on the resonance frequency, the quality factor, or both the resonance frequency and the quality factor. The method may include one or more of the following features, either alone or in combination.

The data may represent S-parameters of the planar resonator. The method may include obtaining additional data based on additional signals output from one or more additional planar resonators arranged in different sectors around the dielectric core. The conduit may be electrically coupled to each of the one or more additional planar resonators to function as a common electrical ground for all planar resonators. The method may include determining resonance frequencies, quality factors, or both resonance frequencies and quality factors of the one or more additional planar resonators based on at least some of the additional data. The method may include identifying content of a sector based on a resonance frequency, a quality factor, or both a resonance frequency and a quality factor of an additional planar resonator corresponding to a sector.

The content may include fluid. Identifying the fluid may include determining a change in the resonance frequency and the quality factor of the planar resonator. Operations to implement obtaining, determining, and identifying may be performed using one or more processing devices. The method may include the one or more processing devices controlling an operation of a system based on the content identified. The system may include a well through a hydrocarbon-bearing formation. Controlling the operation of the system may include controlling one or more components within the well to regulate an amount of hydrocarbon or water in the conduit. Controlling the one or more components may include controlling one or more inflow control devices (ICDs) within the well.

The method may include forming the planar resonator on the dielectric core. Forming the planar resonator on the dielectric core may include using an additive manufacturing process. The planar resonator may be a microwave T-resonator. The planar resonator may be a ring resonator.

Potential advantages of the example systems and methods described in this specification may include reduced cost, increased ease of manufacture, reduced footprint, and increased functionality. For example, implementing planar resonators using additive manufacturing or other printing processes may reduce the size of the resonators and also reduce their cost and complexity. Furthermore, implementations of the system are flexible in that they enable different numbers of planar resonators to be placed within a conduit. As a result, an example system may be implemented as a directional water-fraction sensor that can identify different flow regimes and operate as a water-fraction sensing tool.

Any two or more of the features described in this specification, including in this summary section, may be combined to form implementations not specifically described in this specification.

At least part of the processes, methods, systems, and techniques described in this specification may be controlled by executing, on one or more processing devices, instructions that are stored on one or more non-transitory machine-readable storage media. Examples of non-transitory machine-readable storage media include read-only memory, an optical disk drive, memory disk drive, and random access memory. At least part of the processes, methods, systems, and techniques described in this specification may be controlled using a computing system comprised of one or more processing devices and memory storing instructions that are executable by the one or more processing devices to perform various control operations.

The details of one or more implementations are set forth in the accompanying drawings and the description. Other features and advantages will be apparent from the description and drawings, and from the claims.

DESCRIPTION OF THE DRAWINGS

Like reference numerals in different figures indicate like elements.

DETAILED DESCRIPTION

Figure 1:
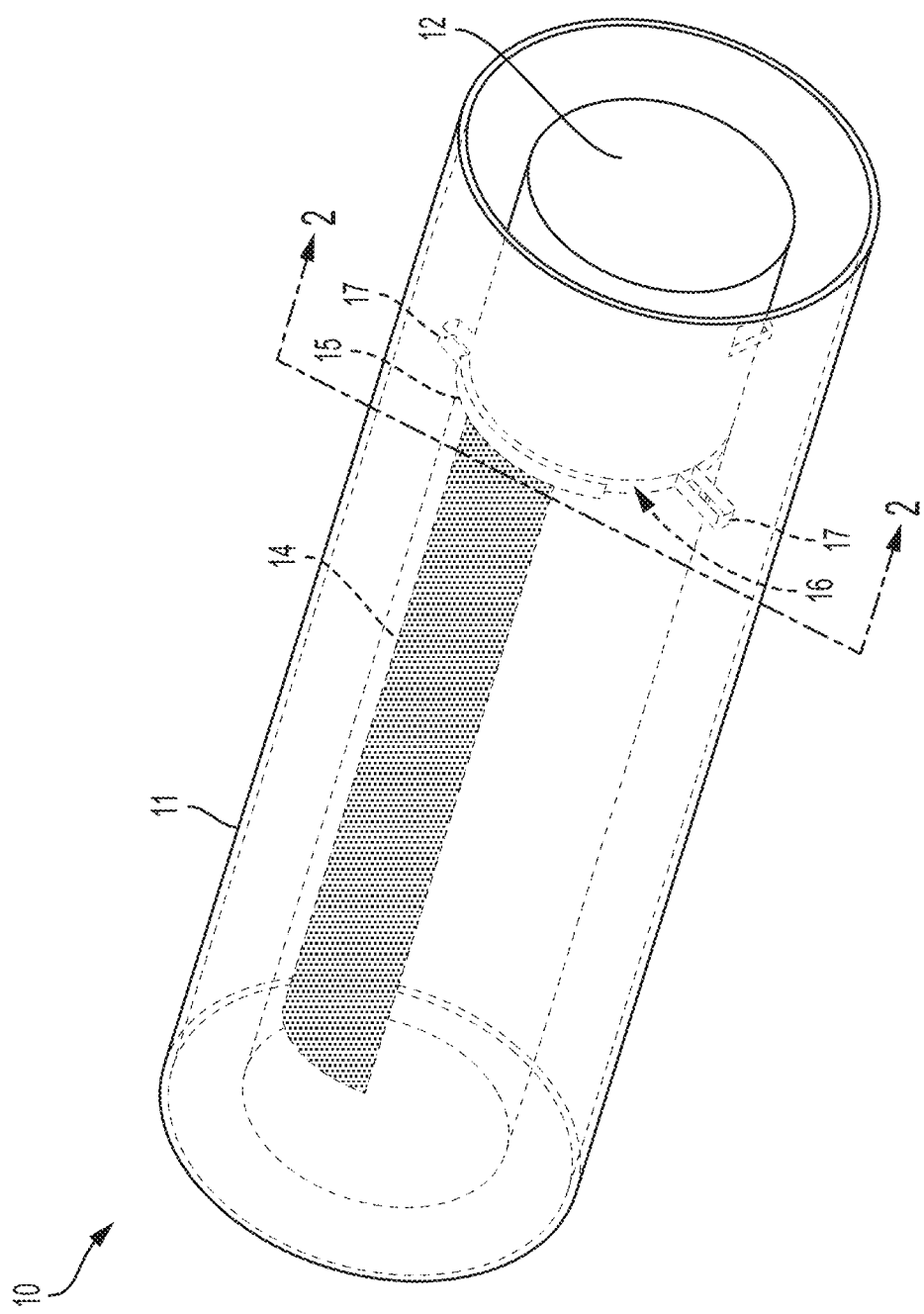
FIG. 1 is a perspective view of components of an example system for identifying content in a conduit.

Described in this specification are example techniques for identifying content in a conduit, such as a pipe made of metal or other electrically-conductive material. The techniques employ a core. In an example, a core is a structure that is configured—for example, shaped and arranged—to fit within the conduit and to hold electrical structures, such as planar resonators. The core be comprised of a dielectric material and may be contained within the conduit. One or more planar resonators, such as a microwave T-resonator, are held on the core.

An example resonator is an electrical device that is configured for oscillation at different frequencies. The frequency of oscillation having the greatest magnitude is the resonant frequency of the resonator. An example planar resonator is a resonator having a flat or substantially flat structure. The example planar resonator includes a feedline and a ground plane. The feedline includes an electrically-conductive material configured to receive and to transmit signals, such as microwave signals. The ground plane is an electrical reference for the feedline.

The planar resonators may be coupled to—for example, physically connected to—the core. In an example, the planar resonators may be formed on the core using an additive manufacturing process, such as three-dimensional (3D) printing, screen printing, or both 3D printing and screen printing. The planar resonators function as sensors for identifying content contained within the conduit. In some examples, each resonator includes a feedline having a ring ground plane. The ring ground plane of the feedline of each planar resonator is coupled to the conduit via a coupling, such as a rod, that is electrically-conductive. This connection is configured to enable the conduit to function as an electrical ground for the planar resonator. In examples where there are multiple planar resonators on the core, the conduit functions as a common electrical ground for the planar resonators. For example, the conduit may function as a common electrical ground for all planar resonators or for some planar resonators on the core.

The system described in the preceding paragraphs may be configured to identify content, such as fluid, gas, or particulate matter contained within, or flowing through, a conduit. For example, the system may be configured to identify a type of the content in the conduit, a geometric distribution of the content in the conduit, a composition of the content, a volumetric proportion of fluids that make up the content, liquid levels of fluids in the content, or some combination of two or more of these characteristics. Generally, the system may be configured to identify any characteristics of the content that can be determined based on the resonance frequency, the quality factor, or both the resonance frequency and the quality factor of one or more of the planar resonators on the core. The quality (Q) factor of the resonator is a value that indicates a level of dampening of the resonator. Resonators having higher quality factors vibrate for greater durations.

In this regard, the planar resonators each may have a resonance frequency and a quality factor that corresponds to content contained within the conduit. In some implementations, the planar resonators each have a resonance frequency that is inversely proportional to the square root of a dielectric constant of the content facing the resonator. This may include all or part of the content in the conduit. The system determines the resonance frequency of each planar resonator and, based on the resonance frequency or frequencies, identifies the content. Similarly, in some implementations, the quality factor of a planar resonator can also be based on the scattering (S) parameters of the planar resonator. S-parameters are values indicating the output response of a resonator on one port (1) of the resonator to an input stimulus on another port (2) of the resonator. The representation of an example S parameter may therefore be "$S_{12}$". The quality factor can be used to identify the dielectric loss of content in the conduit. The dielectric loss may be used to identify, or to estimate, one or more characteristics of the content, such as a volumetric fraction of a gaseous phase of the content, a salinity of the content in cases where the content is fluid, and a temperature of the content.

In some implementations, the system includes hardware, which may include a data processing system, that is configured to obtain data based on signals output from one or more planar resonators on the core. For example, the data may be obtained based on S-parameters transmitted to, and received from, a planar resonator. The data is processed, analyzed, or processed and analyzed to obtain the resonance frequency of the planar resonator, the dielectric loss of the content, or both the resonance frequency of the planar resonator and the dielectric loss of the content. The content is identified based on the resonance frequency, the dielectric loss, or both the resonance frequency and the dielectric loss. For example, if the resonance frequency is within a first frequency range, the content may be identified as oil. For example, if the resonance frequency is within a second, different frequency range, the content may be identified as water or seawater.

As noted, in some implementations, there may be multiple planar resonators spatially distributed around the core. For example, there may be two, three, four, five, six, seven, or eight planar resonators. Each of these planar resonators may be configured to output signals in a sector around the conduit. That is, as described subsequently, signals from each planar resonator may be concentrated in an arc around that planar resonator. In an example, that arc defines a sector associated with a corresponding planar resonator on the core. The resonance frequency of a resonator in each sector may be determined and used to identify the content in each sector. The quality factor of a resonator in each sector may be determined and used to identify the content in each sector. Both the resonance frequency and the quality factor of a resonator in each sector may be determined, and both the resonance frequency and the quality factor may be used to identify the content in each sector. In examples where different sectors contain oil and water, the system may constitute a directional water-fraction sensor that is usable to identify different flow regimes. An example flow regime includes a geometric distribution of different phases of content or of different content inside a conduit.

FIG. 1 shows components 10 of an example system configured to identify content in a conduit. The components include conduit 11. In this example, conduit 11 is a pipe that is made of, or that includes, metal or other electrically-conductive material. For example, the conduit may be made entirely of metal or include a metal strip or ring. For example, metal or metals, such as titanium or steel, that can withstand extreme temperature and pressure conditions within a drilling environment may be used. For example, in oil and gas wells, temperatures in excess of 100° Celsius (C) and pressures in excess of 2000 pounds-per-square-inch (PSI) are considered extreme. In this example, the conduit is cylindrical in shape.

Core 12 is contained within conduit 11. In some implementations, core 12 and conduit 11 are concentric. Core 12 is made of, or includes, a dielectric material. Example dielectrics may have a dielectric loss tangent that is less than 0.01 and a dielectric constant in the range of 2 to 50. Dielectric loss tangents in excess of 0.01, for example, may adversely affect signal output. An example of a dielectric material that may be used includes polyether ether ketone (PEEK). In an example, PEEK has a dielectric loss tangent of 0.005 and a dielectric constant of about 3.2. PEEK may be used because it can withstand temperature and pressure conditions in certain environments, such as drilling environments. In some implementations, core 12 is solid. In some implementations, core 12 is hollow in whole or in part. In some implementations, core 12 includes a single dielectric material. In some implementations, core 12 includes multiple dielectric materials.

In the example of FIG. 1, planar resonator 14 is mounted on the core. In some implementations, planar resonator 14 is formed on core 12 using an additive manufacturing process such as 3D printing, manual screen printing, or a combination of 3D printing and manual screen printing. However, any techniques may be used to mount planar resonator 14 on core 12. Planar resonator 14 may be a microwave resonator, such as a microwave T-resonator or a ring resonator. An example microwave T-resonator is band-stop resonator. An example ring resonator is a band-pass resonator. In some implementations, the resonator has a length in a range between four-to-five times the diameter of the conduit and ten-to-twelve times the diameter of the conduit, inclusive. In some implementations, the planar resonator has a length in a range between one and two meters, inclusive.

In some implementations, the planar resonator is protected on the conduit from surrounding content by a dielectric coating. Example materials for the dielectric coating include oxide ceramics and polymers. Examples of oxides include oxide ceramics of aluminum, titanium, and yttrium. Ceramics, for example, may be sufficiently durable, wear resistant, and corrosion resistant to survive either permanent installation in a well or for five years. Generally, any thin (for example, one millimeter), conformal layer of dielectric material having mechanical and chemical durability and having a small dielectric constant and a small loss tangent may be used. Example dielectrics may have a dielectric loss tangent that is less than 0.01 and a dielectric constant in the range of 2 to 50.

As shown in FIG. 1, planar resonator 14 includes a feedline 15 for receiving input and also includes a ground plane 16 for the feedline. Ground plane 16 is electrically coupled to conduit 11. Any electrically-conductive coupling may be used to implement this electrical connection. In the example of FIG. 1, rods 17 are used. In this example, the rods are made of, or include, an electrically-conductive material that creates a conductive pathway between conduit 11 and planar resonator 14. In this configuration, conduit 11 functions as an electrical ground for planar resonator 14. As described subsequently, conduit 11 may function as a common electrical ground for multiple planar resonators.

Figure 2:
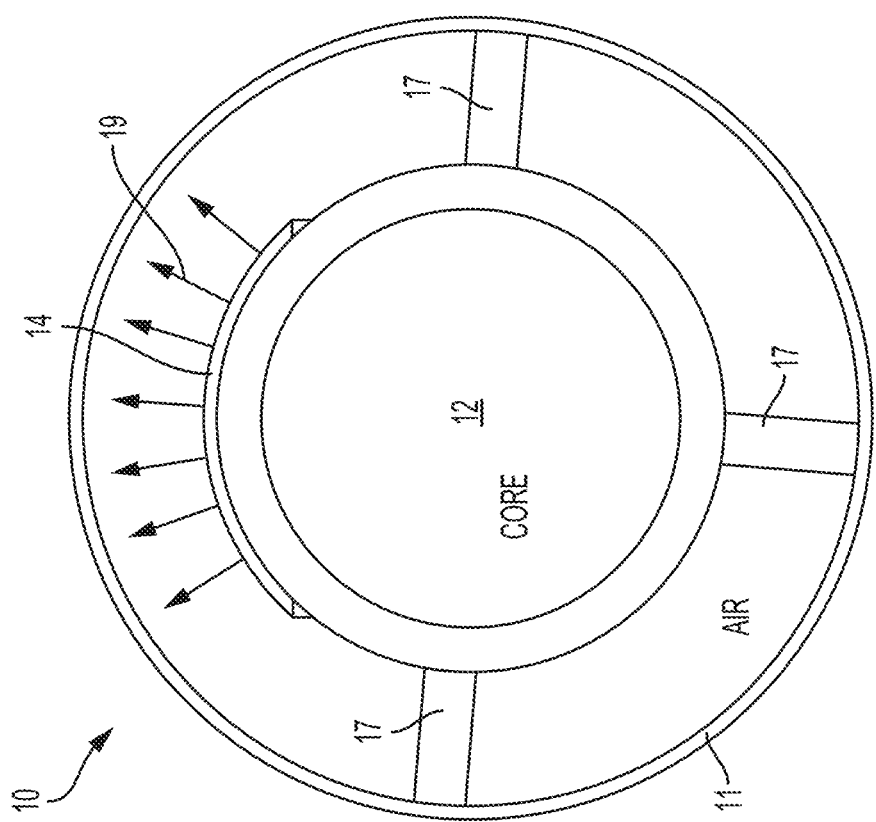
FIG. 2 is a cross-sectional view of components of the example system of FIG. 1 for identifying content—in this example, air—in a conduit.

FIG. 2 shows a cross-section of components 10 taken along line 2-2 of FIG. 1. In FIG. 2, a single planar resonator 14 is on the external surface of core 12 and core 12 is coaxially arranged in the center of conduit 11. In this example configuration, the ring-shaped ground plane of planar resonator 14's feedline is shorted to the conduit 11 using shorting rods 17. As shown in FIG. 2, electrical fields 19 emanating from planar resonator 14 substantially terminate at conduit 11 as a result of its function as electrical ground. In the example of FIG. 2, the content, or medium, in the conduit is air; however, any content may be used instead of air or in addition to air. For example, a valve may be opened to introduce air into the conduit.

In the example of FIGS. 1 and 2, feedline 15 (not visible in FIG. 2) includes a microstrip feedline and the planar resonator includes a quarter-wavelength ($\lambda/4$) shunt stub. In some examples, the dimensions of each feedline and the ground plane may be optimized to match a 50 ohm (Ω) impedance. In some implementations, to match the impedance to 50Ω, the dedicated ring-shaped ground plane 16 is arranged underneath the feedline 15. The feedline and the ring-shaped ground plane ground may be separated by a dielectric. In this example, the dielectric is one millimeter (1 mm) in thickness. Examples of dielectric material that may be used are described previously. The presence of a dielectric content in between the core 12 and the conduit 11 changes the guided wavelength of, and hence the resonance frequency of, planar resonator 14 on core 12.

Figure 3:
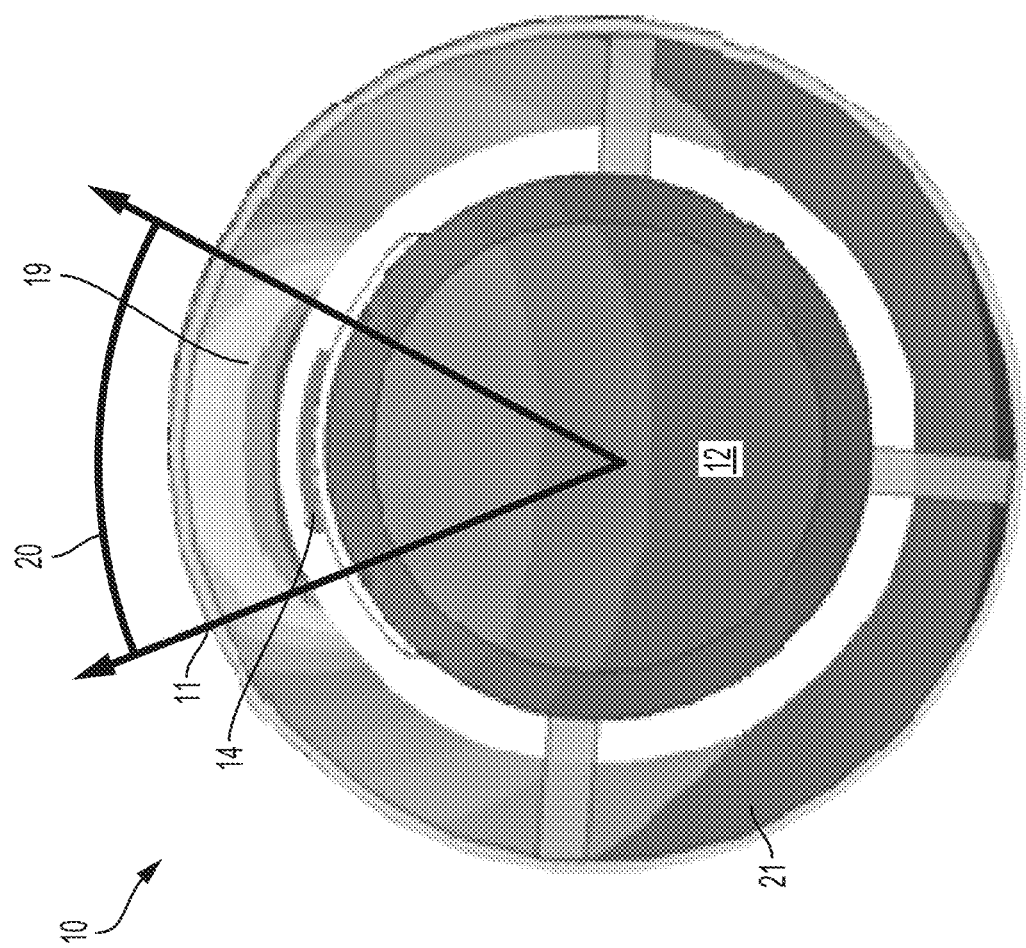
FIG. 3 is a cross-sectional view of components of the example system of FIG. 1 for identifying content in a conduit.

FIG. 3 shows an example electrical field distribution 19 for planar resonator 14 shown in the cross-section of FIG. 2. In the example of FIG. 3, a majority of the electrical field emanating from planar resonator 14 is concentrated in a sector 20—in this example, an arc—between core 12 and conduit 11. In some implementations, the extent of this sector may be 45°, or different than 45°, or may have a shape other than an arc. In this example, the arc is defined relative to a center of a cross-section of the core. In some implementations that include multiple planar resonators, there is a tendency for electrical fields of a single resonator to infringe upon an adjacent sector. As a result, the resonance frequency of a single resonator will be mainly dependent upon the dielectric properties of the content 21 inside its sector, but may also be affected by content in adjacent sectors. To reduce such effects, separators between the sectors may be used, as described subsequently.

Figure 4:
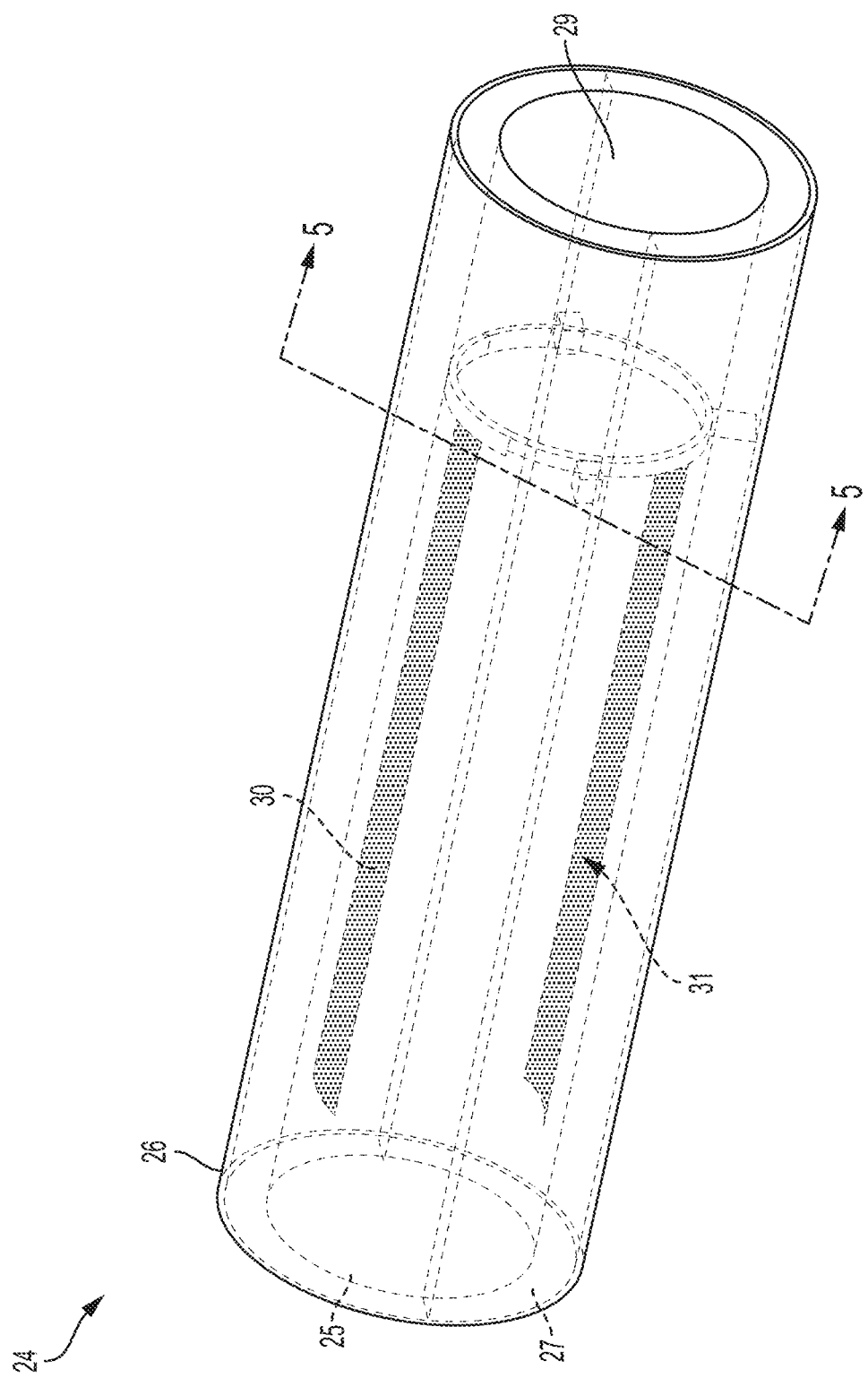
FIG. 4 is a perspective view of components of an example system for identifying content in a conduit.

FIG. 4 shows components 24 of an example system configured to identify a multi-phase flow in a conduit. For example, content in the conduit may be a fluid flow comprised of oil and water. Due to different densities, the oil and water at least partially separate in the conduit. The upper sector 25 of conduit 26 may contain predominantly oil, since oil is less dense than water. The lower sector 27 of conduit 25 may contain predominantly water, since water has a greater density than oil. In this example, the system includes two planar resonators—one facing the upper sector 25 of the conduit and one facing the lower sector 27 of the conduit.

In this example, each sector may be filled with air and then liquid may be introduced into the sectors. As liquid is introduced into a sector, the effective dielectric properties of the sector changes. The change in the effective dielectric properties of the sector changes the effective wavelength of the planar resonator for that sector, which changes the resonance frequency of the planar resonator.

As noted previously, the planar resonators each have a resonance frequency that is inversely proportional to the square root of a dielectric constant of the content facing the resonator—in this example, oil or water. The system therefore determines the resonance frequency of each planar resonator and, based on the resonance frequency or frequencies, identifies the content as either oil or water. The system may also determine the quality factor of each planar resonator and, based on the quality factor or factors, may identify the content as either oil or water. The system may determine both the resonance frequency and the quality factor of each planar resonator and, based on the resonance frequency or frequencies and the quality factor or factors, may identify the content as either oil or water.

The individual components of FIG. 4 may have the same structures and functions as corresponding components of FIG. 1. In this regard, components 24 may include a conduit 26 that is electrically-conductive and a core 29 that is dielectric and that is concentric with the conduit. The system of FIG. 4 includes first planar resonator 30 and second planar resonator 31. First planar resonator 30 faces the upper sector 25 of the conduit and second planar resonator 31 faces the lower sector 27 of the conduit. In some implementations, there may be more than two planar resonators and arrangement of the planar resonators may be different than that shown in FIG. 4. The first and second planar resonators may be of the same type as, and have the same structure and function as, planar resonator 14 of FIG. 1. Each of the first and second planar resonators 30 and 31 may be electrically coupled to conduit 26 in the same way that planar resonator 24 is electrically coupled to conduit 11 in FIG. 1. For example, first planar resonator 30 may be electrically coupled to conduit 26 by couplings, such as rods 32 in FIG. 5. For example, second planar resonator 31 may be electrically coupled to conduit 26 by couplings, such as rods 32 in FIG. 5. Different couplings, for example separate rods, may be used to electrically couple—for example, to electrically connect—different resonators to the conduit. For example, each resonator may have its own rod or set of rods that it uses for electrical coupling to the conduit. In this configuration, conduit 26 functions as a common electrical ground for both first planar resonator 30 and second planar resonator 31. In this example, the common electrical ground defined by the conduit surrounds the first and second planar resonators.

Figure 5:
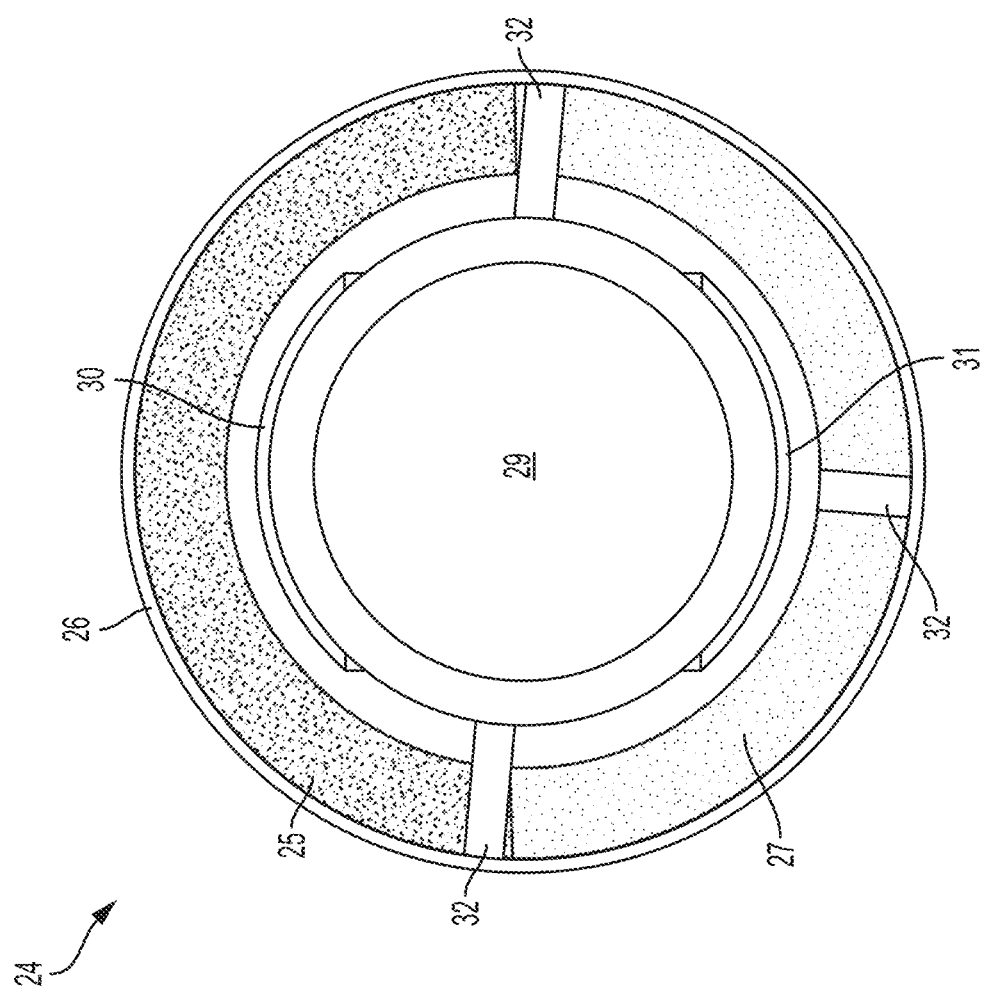
FIG. 5 is a cross-sectional view of components of the example system of FIG. 4 for identifying content in a conduit.

In this regard, FIG. 5 shows a cross-section of components 24 taken along line 5-5 of FIG. 4. In this example, the electrical fields emanating from the each resonator substantially terminate at conduit 26 as a result of its function as electrical ground. In the example of FIG. 5, the content, or medium, on the upper sector 25 of the conduit is oil and the content, or medium, on the lower sector 27 of the conduit is water. However, any content may be used.

Figure 6:
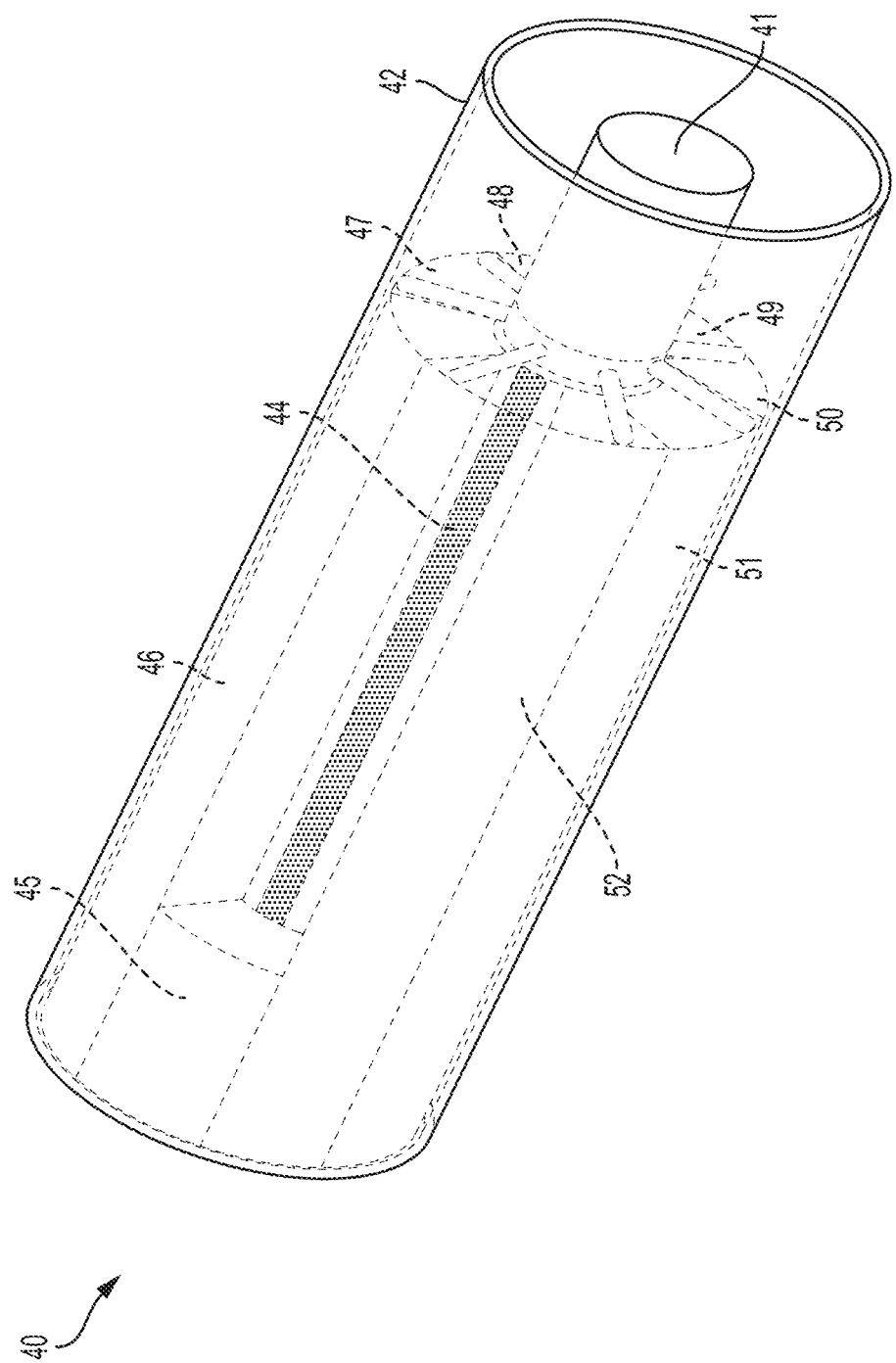
FIG. 6 is a perspective view of components of an example system for identifying content in a conduit.

As explained previously, in some implementations, a system for identifying content in a conduit may include more than two planar resonators. In example system 40 of FIG. 6, there are eight planar resonators arranged around a core 41. The eight planar resonators are configured to identify a multi-phase flow in conduit 42. Individual components of the system may have the same structures and functions as corresponding components of FIGS. 1 through 5. For example, the components may include conduit 42 that is electrically-conductive and core 41 that is dielectric and that is concentric with the conduit. Of the eight resonators included in the system of FIG. 5, only one can be seen: planar resonator 44. In the figure, part of sector 45 is not shown to reveal part of planar resonator 44. Sectors associated with each corresponding planar resonator include sectors 45, 46, 47, 48, 49, 50, 51, and 52. Rods (not labeled) electrically connect corresponding planar resonators to conduit 42. Different couplings, for example separate rods, may be used to electrically couple—for example, to electrically connect—different resonators to the conduit. Conduit 42 thus functions as a common electrical ground for all of the eight planar resonator contained within system 40.

In some implementations that include more than one planar resonator, there may be separators that define the individual sectors. In some implementations, the separators may be metallic. As such, the separators may provide electromagnetic isolation between neighboring sectors to enable independent characterization of content in each sector. In some implementations, the separators may be made of another material, such as a dielectric material. The separators may be or include sheets that may be located on each side of a corresponding resonator between the conduit and the core. The sheets may form an air-tight or liquid-tight seal between the core and the conduit. Thus, by configuring the sheets, the content of a sector can be isolated in whole or in part from the content of other sectors, including sectors that are immediately adjacent. Metallic sheets also may be configured to confine in whole or in part electrical fields within their respective sectors. As such, in some implementations, the resonance frequency of each planar resonator will be defined by the dielectric medium in its sector only.

In an example implementation, most of the electrical fields of a planar resonator are concentrated in an arc around a 10 mm wide resonator (λ/4 stub) having a resonant frequency in the range of 50 megahertz (MHz) to 200 MHZ. In this example, each resonator may cover at least a 45° sector of a cross-section of the conduit in which content is to be identified. In order to cover the entire 360° arc of the conduit, eight planar resonators are arranged on the core, as in FIG. 6. The planar resonators face in different directions and, therefore, cover the different sectors. The system is thus configured to characterize the fluid composition in different directions. As a result, the system may identify a flow regime in a multiphase flow, such as measuring a water fraction in oil.

Figure 14:
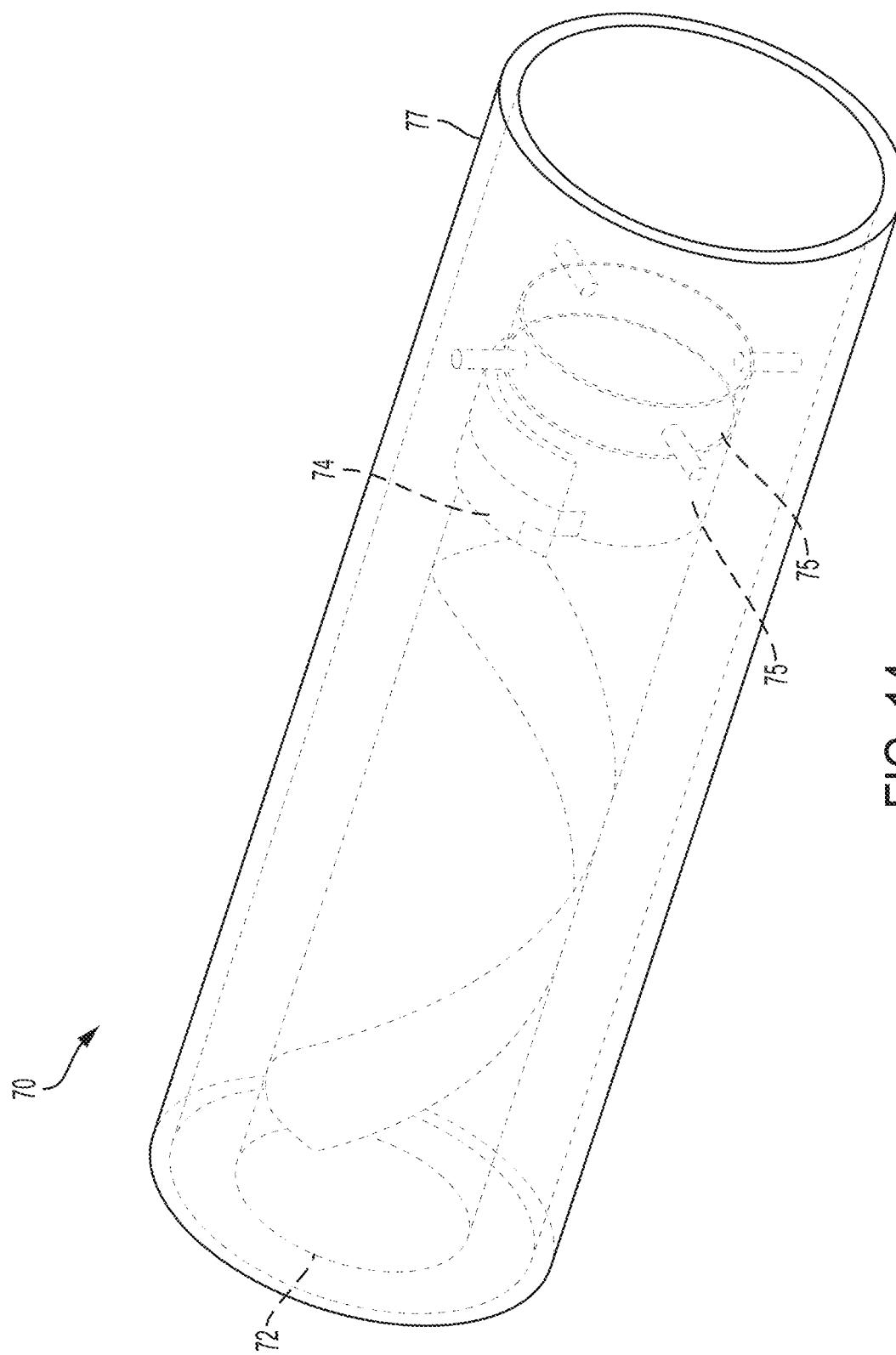
FIG. 14 is a perspective view of a spiral T-resonator.

In some implementations, a system for identifying content in a conduit may include a microwave spiral T-resonator. An example of a microwave spiral T-resonator 70 is shown in FIG. 14. Spiral T-resonator 70 is mounted on a core 72. In some implementations, spiral T-resonator 70 is formed on core 72 using an additive manufacturing process such as 3D printing, manual screen printing, or a combination of 3D printing and manual screen printing.

Spiral T-resonator 70 includes a feedline 74 having a ring ground plane 75. Feedline 74 is wrapped spirally around core 72 as shown in FIG. 14. Ground plane 75 is electrically coupled to conduit 77. Any electrically-conductive coupling may be used to implement this electrical coupling. In the example of FIG. 14, rods 78 are used. As described, the rods may be made of or include an electrically-conductive material that creates a conductive pathway between conduit 77 and spiral T-resonator 70. In this configuration, conduit 77 functions as an electrical ground for spiral T-resonator 70. In some implementations, there may be multiple spiral T-resonators mounted on the core. Conduit 77 may function as a common electrical ground for multiple spiral T-resonators in the manner described previously.

Each planar resonators may be calibrated prior to use. An example method of performing the calibration includes examining a response of a resonator—for example, a shift in resonance frequency for content levels of known liquids having known dielectric properties. Curve fitting techniques may then be used to associate the resonator responses with corresponding dielectric constants. A relationship can be established between each dielectric constant, which corresponds a content in the conduit, and a characteristic curve of the planar resonator. Before operation, the resonator response can be measured at two or three known liquid levels, which may act as calibration points for the resonator for subsequent readings.

Figure 7:
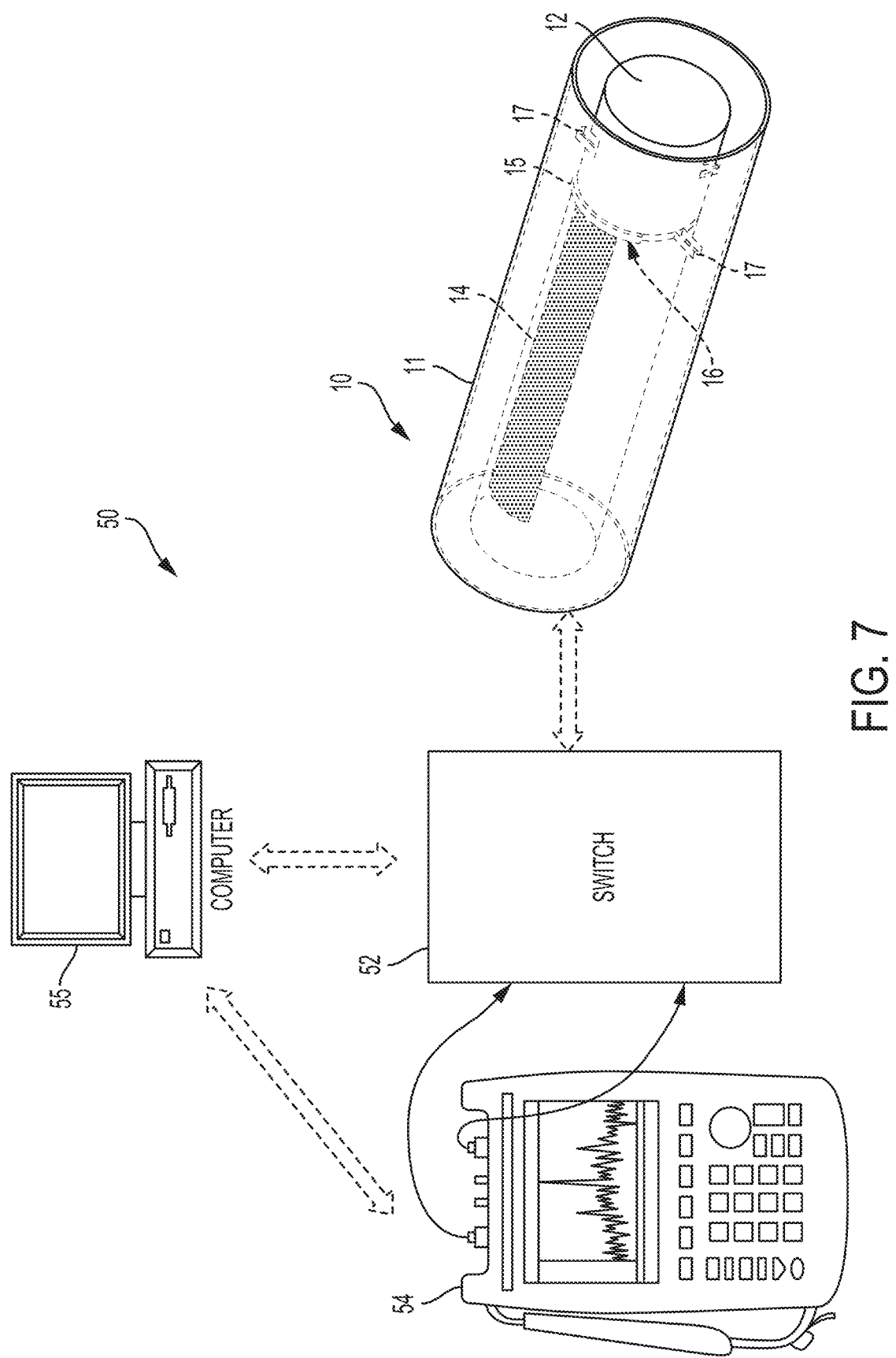
FIG. 7 is an example diagram showing components, including a data processing system, of an example system for identifying content in a conduit.

FIG. 7 shows an example system 50 that may include the components of any of FIGS. 1 through 6. Components 10 of FIG. 1 are used as an example. In example system 50, the resonance frequency of each planar resonator may be measured using a vector network analyzer (VNA) or other electronic component, such as a microwave oscillator, that is electrically coupled to the planar resonators. VNA 54 may be implemented as a stand-alone instrument as shown or as part of a data processing system. VNA 54 is configured to receive, via switch 52, signals from each of the microwave resonators. In this example, the VNA is configured to observe the band-pass or band-stop response of the planar resonators.

In example system 50, switch 52 is configured to connect each of the planar resonators on the core to VNA 54 in turn. Where only one resonator is included, as in the example of FIG. 7, the switch may be controlled to connect and to disconnect that resonator. The switch may be controlled by a computing system, such computing system 55. Computing system 55 may include one or more processing devices, such as microprocessors. Examples of computing systems that may be used include those described in this specification. Computing system 55 may be configured—for example, programmed—to communicate with VNA 54 and switch 52, as represented by the dashed arrows. Signal transmissions between components 10 and switch 52 are also represented by a dashed arrow System 50, including VNA 54, may be configured to capture raw microwave resonance data from the planar resonators on the core, to perform conversions on the data, and to process the data to identify content within the conduit. In an example, the system may be configured to obtain data based on signals output from each planar resonator on the core, to determine a resonance frequency of each planar resonator based on the data, and to identify the content of different sectors around the core based on the resonance frequencies. In an example, the system may be configured to obtain data based on signals output from each planar resonator on the core, to determine a quality factor of each planar resonator based on the data, and to identify the content of different sectors around the core based on the quality factors. In an example, the system may be configured to obtain data based on signals output from each planar resonator on the core, to determine a resonance frequency and a quality factor of each planar resonator based on the data, and to identify the content of different sectors around the core based on both the resonance frequencies and the quality factors. As noted, in some implementations, the data may be obtained based on S-parameters transmitted from, or received by a planar resonator under consideration.

Incident microwaves superimposed onto reflected microwaves cause destructive interference at the resonance frequency. At this frequency, microwaves are not passed from one port of a resonator to another port of the resonator. As a result, when a microwave resonator, such as planar resonator 14, is operating, and indiscernible signals or undetectable signals are identified for that microwave resonator at VNA 54, system 50 may determine that the frequency at which that microwave resonator is operating is the resonant frequency of that microwave resonator. An undetectable signal may be identified based on knowledge that the microwave resonator is operating and that a signal should be received as a result of the microwave resonator operating, but that the signal has not been received. The system may use this detected resonance frequency to identify the content in the sector associated with the planar resonator. For example, computing system 55 may access a database that correlates resonance frequencies to identities of content. Computing system 55 may then provide the identity of the content associated with the detected resonance frequency. For example, the identity may be sent out over a network or displayed on a display screen.

In implementations used in the petroleum industry, levels of oil and water in a conduit may be determined. Those determined levels may be used to affect operation of a well through, or to, a hydrocarbon-bearing formation. For example, the computing system may control one or more components within the well to regulate an amount of oil or water in a conduit within the well. Controlling the one or more components may include controlling one or more inflow control devices (ICDs) within the well. In this regard, ICDs may include valves that control the flow of fluid produced from a formation into a wellbore. This fluid, which may be referred to as production fluid, may contain varying amounts of water and oil (or other hydrocarbon). Areas in which the amount of water in the fluid exceeds a predefined level may be referred to as water cut zones. The example systems described in this specification may be used for analyzing the fluid entering an ICD to determine the amount of water entering the ICD and to identify the water cut zone based on the amount of water. The computing system may close, or may direct closure of, an ICD in response to identifying a water cut zone within a well.

Operational controls may be implemented directly by the computing system absent human intervention or the operational controls may be directed by the computing system and implemented through human intervention. Reflectance-based oscillator arrangements other than those of FIG. 7 or transmittance-based oscillator arrangements other than those of FIG. 7 may also be used to identify the content in a conduit using one or more planar resonators.

The following are example methods that may be used by computing system 55 to identify resonance frequencies of one or more planar resonators. For example, computing system 55 may monitor frequencies output by a planar resonator. Computing system 55 may generate graphs of those frequencies and identify a resonance frequency by a decrease in frequency magnitude that produces a minimum frequency value for the resonator. As explained previously, the magnitude of the resonance frequency is based on the content through which the electrical fields of the planar resonator pass. As the content inside the conduit—that is, the content around the core—changes from air to oil or water for example, a change in resonance frequency occurs.

Figure 8:
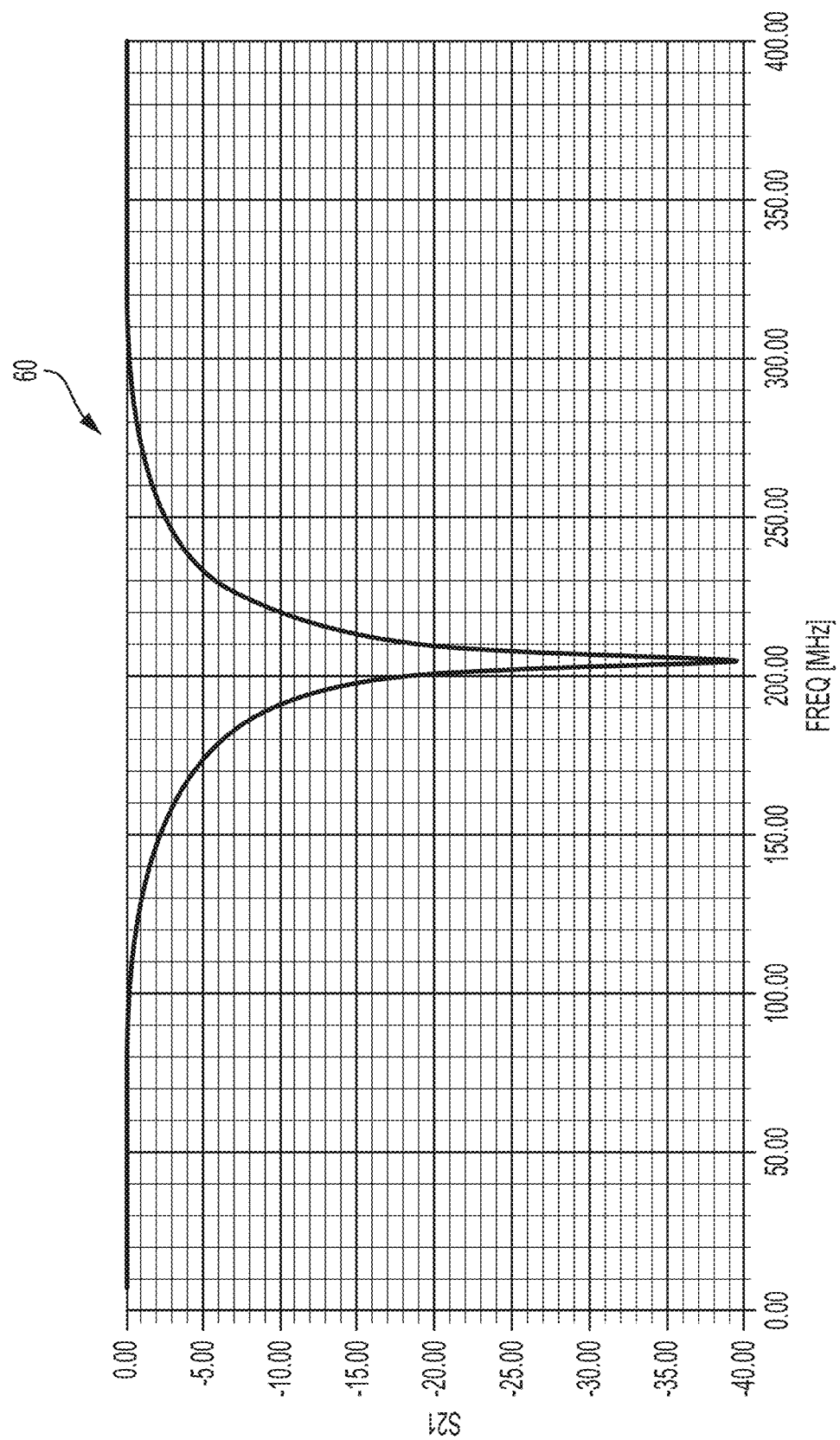
FIG. 8 is a graph showing, for air, the frequency of a planar resonator in megahertz plotted against an S-parameter ($S_{21}$) of the planar resonator.

Referring back to FIG. 2, in that example, a single planar resonator 14 is used and the content in conduit 11 is air. FIG. 8 is a graph 60 showing the frequency output of planar resonator 14 in megahertz plotted against an S-parameter ($S_{21}$) of planar resonator 14. As shown in FIG. 8, for air, a decrease occurs at 204.6 MHz. The resulting minimum represents the resonance frequency of planar resonator 14.

Figure 9:
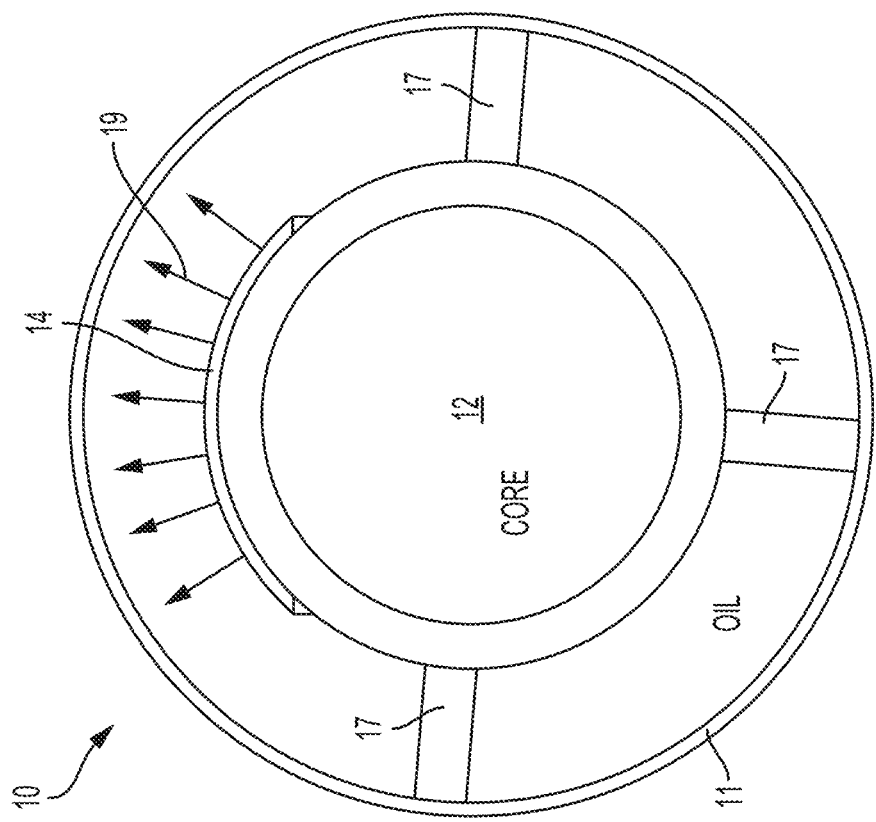
FIG. 9 is a cross-sectional view of components of the example system of FIG. 1 for identifying content—in this example, oil—in a conduit.
Figure 10:
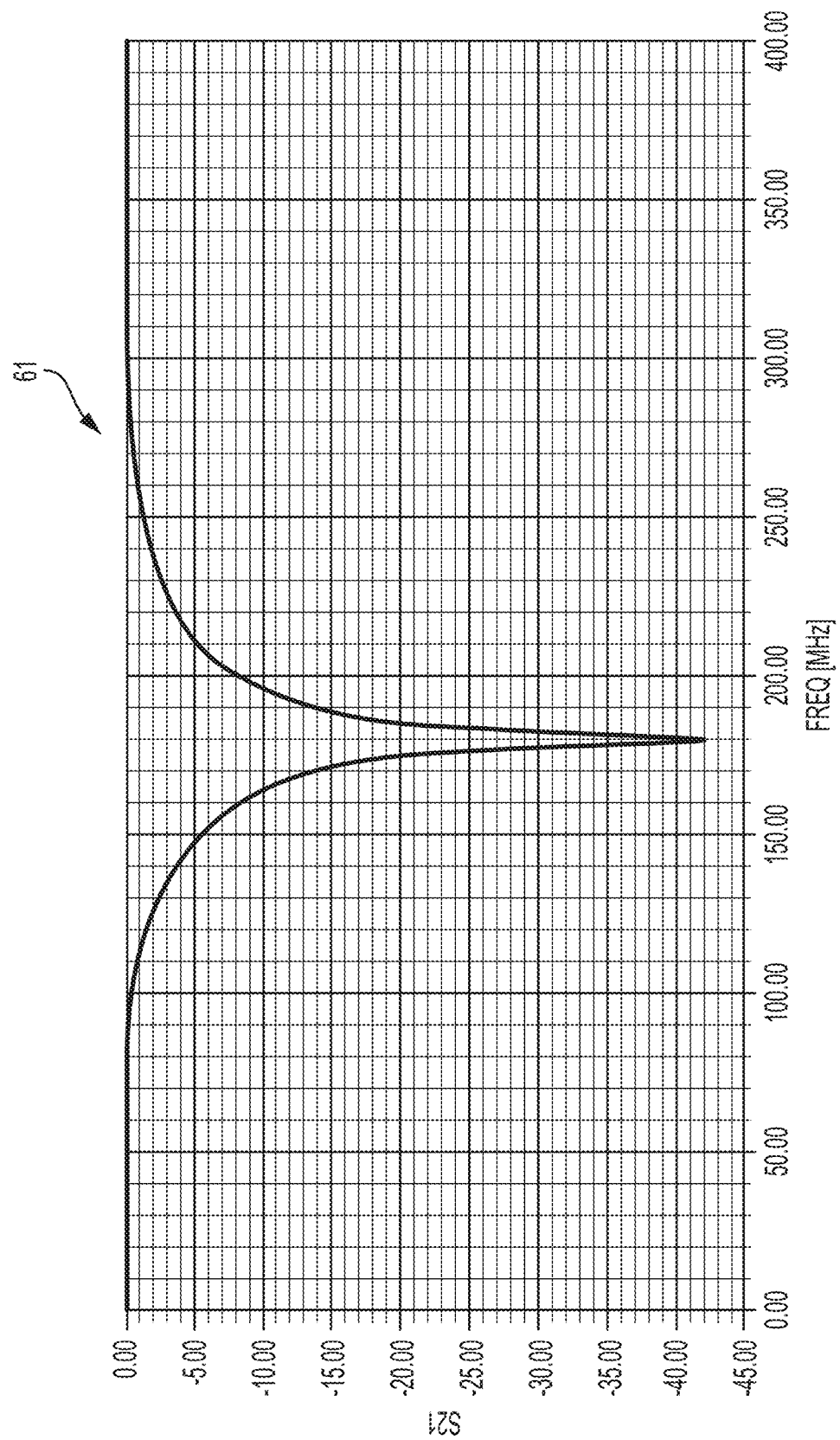
FIG. 10 is a graph showing, for oil, the frequency of a planar resonator in megahertz plotted against an S-parameter ($S_{21}$) of the planar resonator.

In the example of FIG. 9, a single planar resonator 14 is used and the content in conduit 11 is oil. FIG. 10 is a graph 61 showing the frequency output of planar resonator 14 in megahertz plotted against an S-parameter of planar resonator 14. As shown in FIG. 10, for oil, a decrease occurs at 179.7 MHz. The resulting minimum represents the resonance frequency of planar resonator 14. Thus, the resonance frequency of the planar resonator decreases from 204.6 MHz to 179.7 MHz as the dielectric constant of the content around the core increases from 1.0 (for air) to 2.2 (for oil).

Figure 11:
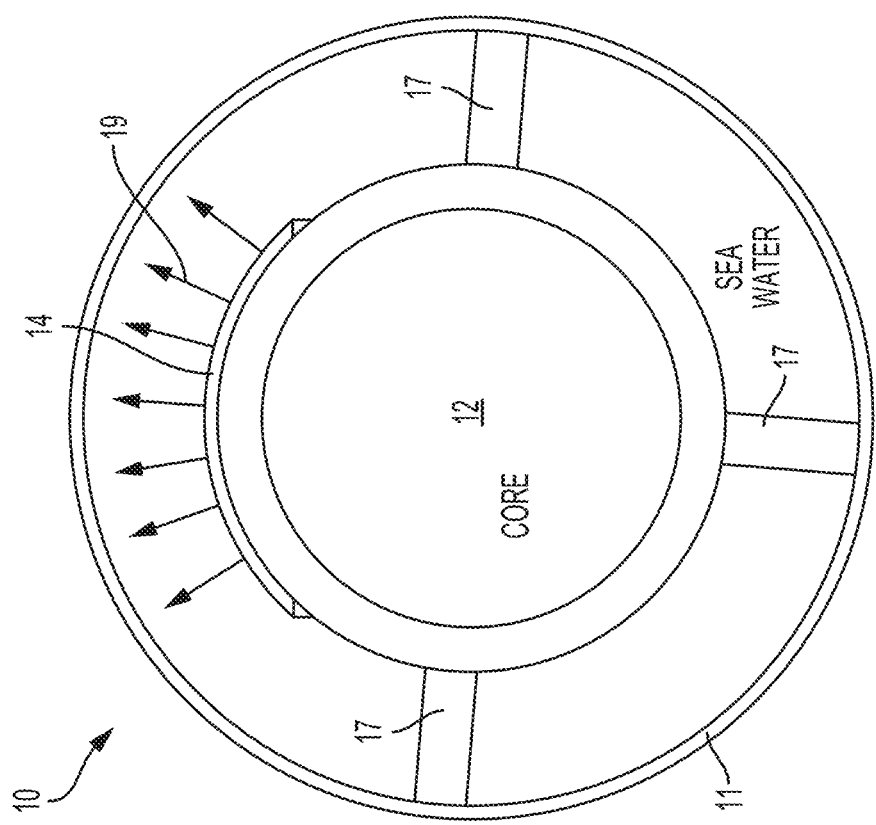
FIG. 11 is a cross-sectional view of components of the example system of FIG. 1 for identifying content—in this example, seawater—in a conduit.
Figure 12:
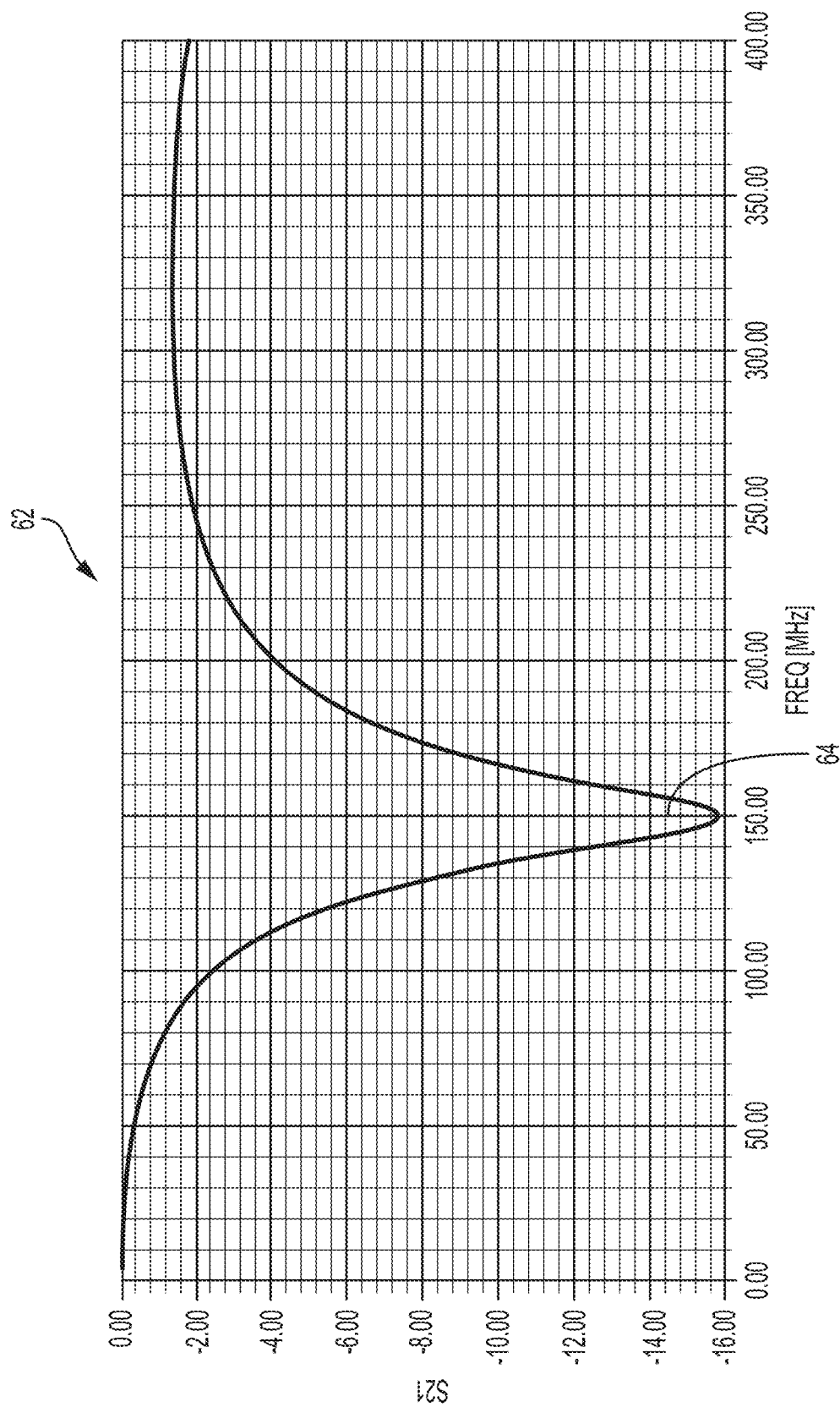
FIG. 12 is a graph showing, for seawater, the frequency of a planar resonator in megahertz plotted against an S-parameter ($S_{21}$) of the planar resonator.

In the example of FIG. 11, a single planar resonator 14 is used and the content in conduit 11 is seawater. FIG. 12 is a graph 62 showing the frequency output of planar resonator 14 in megahertz plotted against an S-parameter of planar resonator 14. As shown in FIG. 12, for seawater, a decrease occurs at 149.2 MHz. The resulting minimum represents the resonance frequency of planar resonator 14. Thus, the resonance frequency of planar resonator 14 decreases from 179.7 MHz to 149.2 MHz as the dielectric constant of the content around the core increases from 2.2 (for oil) to 80.0 (for seawater). Accordingly, when the water fraction in the conduit changes from 100% oil to 100% water, the resonance frequency of the planar resonator also changes in to 149.2 MHz from 179.7 MHz. In FIG. 12, there is wider gap 64 in the resonance frequency curve than in FIGS. 8 and 10 because the content is seawater, and seawater is more lossy than air or oil.

Figure 13:
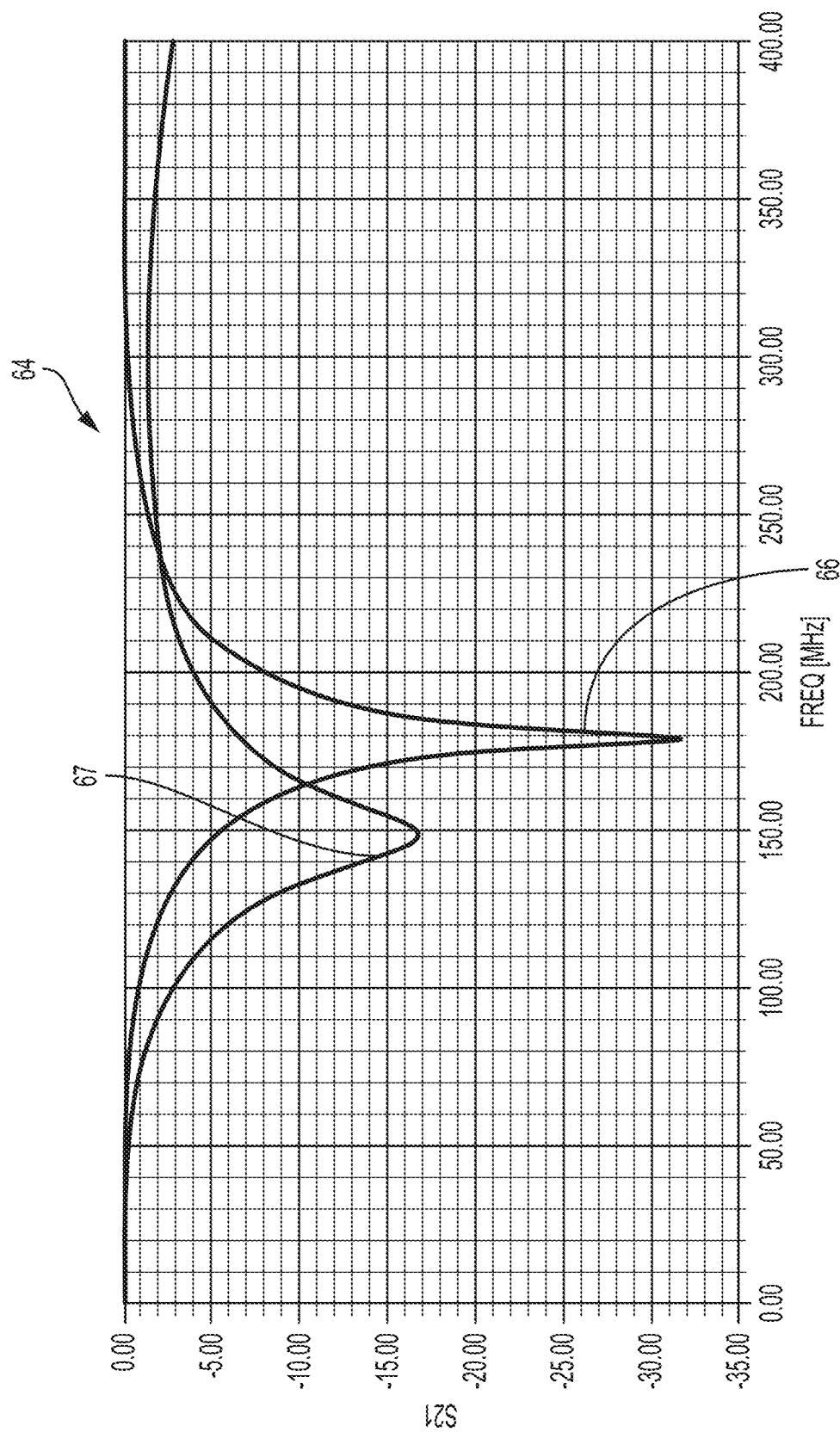
FIG. 13 is a graph showing resonant frequencies of two planar resonators in megahertz plotted against an S-parameter ($S_{21}$) of the planar resonators.

Referring to the example of FIG. 4, two planar resonators are used—one planar resonator 31 facing water in the conduit and one planar resonator 30 facing oil in the conduit. This configuration may be used to implement directional water fraction sensing. Directional water fraction sensing may include identifying sectors in a cross-section of the conduit that contain water or a percentage of water sufficient to affect resonance. In this example, most of the electrical fields from planar resonator 30 will be in upper sector 25 of the conduit cross-section (of FIG. 5) and most of the electrical fields of planar resonator 31 will be in the lower sector 27 of the conduit cross-section. Accordingly, the system can distinguish the content in the upper sector from the content in the lower sector. In this regard, FIG. 13 is a graph 64 showing the frequencies outputs of planar resonators 30, 31 in megahertz plotted against an S-parameter of the planar resonators. As shown in FIG. 13, curve 66 shows the resonance response for planar resonator 30 facing oil in the upper sector of the conduit. The resonance frequency for oil is known to be 179.7 MHz, which is close to the 178.9 MHz resonance frequency of curve 66. In FIG. 13, curve 67 shows the resonance response for planar resonator 31 facing water in the lower sector of the conduit. The resonance frequency for water is known to be 149.2 MHz, which is close to the 148.2 MHz resonance frequency of curve 67.

The known magnitudes of the resonance frequencies for different content may be stored in memory in computing system 55 or in any other computer memory. Computing system may compare known magnitudes to the detected magnitudes and, if the two are within an acceptable tolerance, declare the content associated with the detected magnitude to be the content associated with the known magnitude. In the example of FIG. 13, the content producing 178.9 MHz resonance frequency may be declared to be oil, and the content producing 148.2 MHz resonance frequency may be declared to be water.

Thus, the example system can sense how content, such as oil and water, is distributed in the cross-section of a conduit. For example, in FIG. 4, the upper sector contains 100% oil while the lower sector contains 100% water. So, the system can determine that the absolute water-cut (that is, the percentage of water in the fluid) is 50%. The system can also determine that the content in the upper sector is 100% oil and the content in the lower sector is 100% water. As explained, the system may use more than the two planar resonators—see, for example, FIG. 6—to increase directional sensing resolution.

The resonance frequencies or quality factors obtained by the data processing system may be based on one or more real-time measurements. In this regard, in some implementations, real-time may not mean that two actions are simultaneous, but rather may include actions that occur on a continuous basis or track each other in time, taking into account delays associated with processing, data transmission, hardware, and the like.

The example systems described in this specification may be implemented for wells that are vertical or for wells that are, in whole or part, non-vertical. For example, the system may be used to analyze content in pipes of a deviated well, a horizontal well, or a partially-horizontal well.

The example systems described in this specification employ microwave resonators, as explained previously. However, the systems are not limited to use with microwaves. Electromagnetic waves and electromagnetic wave resonators may be used in place of the microwave resonators. For example, radio frequencies (RF) and radio frequency resonators may be used instead of microwave frequencies and microwave frequency resonators. In an example, radio frequencies extend about from 3 Hertz (Hz) to 300 GigaHertz (GHz). In an example, microwave frequencies extend about from 0.3 GHz to 300 GHz.

The operational frequencies of the systems described in this specification are not limited to any specific frequency band. The frequencies may be increased or decreased based upon the size, dimensions, or both of the conduit and planar resonators used.

Examples described in this specification relate to the petroleum industry. However, the example systems described in this specification are not limited to the petroleum industry and may be used in any appropriate context. The systems may be used to identify various types of content, such as fluid, in a conduit. For example, the systems may be used in industries to automate processes involving transmission of chemicals, or in medical or other industrial applications. In the context of drilling, the systems may be used in various locations, such as in a wellhead or downhole. The systems may be used in a laboratory as well.

All or parts of the methods, systems, and techniques described in this specification may be controlled using a computer program product. The computer program product may include instructions that are stored on one or more non-transitory machine-readable storage media. The instructions may be executable on more or more processing devices. A computer program can be written in any form of programming language, including compiled or interpreted languages. A computer program can be deployed in any form, including as a stand-alone program or as a module, part, subroutine, or other unit suitable for use in a computing environment. A computer program can be deployed to be executed on one computer or on multiple computers at one site or distributed across multiple sites and intercoupled by a network.

Actions associated with controlling the systems can be performed by one or more programmable processors executing one or more computer programs to control all or some of the operations described previously. All or part of the systems can be controlled by special purpose logic circuitry, such as an FPGA (field programmable gate array), an ASIC (application-specific integrated circuit), or both an FPGA and an ASIC.

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, such as magnetic, magneto-optical disks, or optical disks. Non-transitory machine-readable storage media suitable for embodying computer program instructions and data include all forms of non-volatile storage area, including by way of example, semiconductor storage area devices, such as EPROM (erasable programmable read-only memory), EEPROM (electrically erasable programmable read-only memory), and flash storage area devices; magnetic disks, such as internal hard disks or removable disks; magneto-optical disks; and CD-ROM (compact disc read-only memory) and DVD-ROM (digital versatile disc read-only memory).

Any "electrical connection" as used in this specification may imply a direct physical connection or a connection that includes, or does not include, intervening components (such as air) but that nevertheless allows electrical signals to flow between coupled components. Any "connection" involving electrical circuitry that allows signals to flow, unless stated otherwise, is an electrical connection and not necessarily a direct physical connection regardless of whether the word "electrical" is used to modify "connection".

Elements of different implementations described may be combined to form other implementations not specifically set forth previously. Elements may be left out of the systems described without adversely affecting their operation or the operation of the system in general. Furthermore, various separate elements may be combined into one or more individual elements to perform the functions described in this specification.

Other implementations not specifically described in this specification are also within the scope of the following claims.

What is claimed is:

1. A system comprising:
   a core comprised of a dielectric material;
   a planar resonator on the core;
   a conduit containing the core and the planar resonator, the conduit comprising an electrically-conductive material; and
   a coupling that is electrically-conductive and that connects the planar resonator to the conduit to enable the conduit to function as an electrical ground for the planar resonator,
   where the core and the conduit are concentric,
   where the core is solid, and
   where the electrical field emanating from the planar resonator is concentrated in a sector between the core and the conduit.

2. The system of claim 1, where the planar resonator comprises a microwave T-resonator,
   where the planar resonator comprises a feedline comprising a ring ground plane, and
   where the ring ground plane is coupled to the conduit via an electrically-conductive rod creating a conductive pathway between the conduit and the planar resonator to enable the conduit to function as an electrical ground for the planar resonator.

3. The system of claim 1, where the planar resonator comprises:
   a spiral T-resonator;
   a quarter-wavelength shunt stub; and
   a microstrip feedline,
   where the planar resonator is protected on the conduit from surrounding content by a dielectric coating, and
   where the dielectric coating comprises oxide ceramics and polymers.

4. The system of claim 1, where the planar resonator comprises material printed onto the core,
   where the dielectric material comprises a dielectric loss tangent that is less than 0.01,
   where the dielectric material comprises a dielectric constant from two (2) to fifty (50), and
   where the dielectric material comprises a polyether ether ketone (PEEK) material.

5. The system of claim 1, where the conduit comprises a pipe that is made of metal.

6. The system of claim 1, where the conduit comprises a metallic pipe allowing it to function as electromagnetic shielding for the planar resonator,
where the planar resonator is formed on the core using an additive manufacturing process, and
where the additive manufacturing process comprises at least one of three-dimensional (3D) printing and screen printing.

7. The system of claim 1, further comprising:
a computing system to obtain data from the planar resonator, to obtain a resonance frequency of the planar resonator based on the data, and to identify a content of the conduit based on the resonance frequency.

8. The system of claim 1, where a content of the conduit comprises fluid,
where identifying the fluid comprises determining a change in the resonance frequency or a quality factor of the planar resonator, and
where the planar resonator comprises a length from four (4) times the diameter of the conduit to twelve (12) times the diameter of the conduit.

9. The system of claim 1, where the planar resonator is a first planar resonator and the coupling is a first coupling; and
where the system further comprises:
one or more additional planar resonators spatially distributed on the core; and
one or more additional couplings, each of the one or more additional couplings being electrically-conductive and connecting the conduit to a corresponding additional planar resonator to enable the conduit to function as the electrical ground for the corresponding additional planar resonator.

10. The system of claim 9, where the one or more additional planar resonators comprise between one additional planar resonator and seven additional planar resonators.

11. The system of claim 9, where the one or more additional planar resonators are on a plurality of different sectors of the core.

12. The system of claim 1, further comprising:
one or more metallic separators within the conduit, the one or more metallic separators for confining fluid within volumes corresponding to a plurality of individual sectors of the core,
where the core is solid.

13. The system of claim 1, further comprising a vector network analyzer electrically coupled to the planar resonator; where a resonance frequency of the planar resonator decreases from 204.6 MHz to 179.7 MHZ as the dielectric constant of content in the conduit increases from 1.0 (for air) to 2.2 (for oil), and
where the resonance frequency is determined using the vector network analyzer.

14. The system of claim 1, where the planar resonator comprises a feedline comprising a ring ground plane,
where the ring ground plane is arranged underneath the feedline,
where the ring ground plane and the feedline are separated by a dielectric material, and
where the dielectric material is one millimeter (1 mm) in thickness.

15. The system of claim 1, further comprising one or more separators within the conduit,
where the one or more separators comprises sheets disposed on each side of the planar resonator between the conduit and the core,
where the sheets form at least one of an air-tight seal and a liquid-tight seal between the core and the conduit.

16. The system of claim 1, where a resonance frequency of the planar resonator decreases from 179.7 MHz to about 149.2 MHZ as the dielectric constant of content in the conduit increases from 2.2 (for oil) to 80.0 (for seawater).

17. The system of claim 16, where the resonance frequency is determined using a vector network analyzer that is electrically coupled to the planar resonator.

18. A system comprising:
a core comprised of a dielectric material;
a planar resonator on the core;
a conduit containing the core and the planar resonator, the conduit comprising an electrically-conductive material; and
a coupling that is electrically-conductive and that connects the planar resonator to the conduit to enable the conduit to function as an electrical ground for the planar resonator,
where the core and the conduit are concentric,
where the planar resonator comprises a ring resonator,
where the electrical field emanating from planar resonator is concentrated in a sector between the core and the conduit,
where the sector is an arc, and
where the extent of the sector is 45 degrees.

* * * * *